US006261844B1

(12) United States Patent
Smith et al.

(10) Patent No.: US 6,261,844 B1
(45) Date of Patent: Jul. 17, 2001

(54) URINE PRESERVATIVE

(75) Inventors: Scott M. Smith, League City; Jeannie L. Nillen, Houston, both of TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/213,988

(22) Filed: Dec. 17, 1998

(51) Int. Cl.$^7$ .................................................. G01N 33/493
(52) U.S. Cl. .................. 436/18; 436/8; 252/380; 252/397; 422/40
(58) Field of Search .................. 436/18, 8; 252/380, 252/397; 422/40

(56) References Cited

U.S. PATENT DOCUMENTS

| 3,887,701 | * | 6/1975 | Nachtigal | 424/54 |
| 4,200,651 | | 4/1980 | Griffith | 424/320 |
| 4,258,032 | | 3/1981 | Mehl | 424/148 |
| 4,336,880 | | 6/1982 | Mehl | 206/524.4 |
| 4,666,896 | | 5/1987 | Warner, Jr. et al. | 514/114 |
| 4,847,079 | | 7/1989 | Kwan | 424/85.7 |
| 4,863,989 | | 9/1989 | Obayashi et al. | 524/419 |
| 4,972,019 | | 11/1990 | Obayashi et al. | 524/83 |

OTHER PUBLICATIONS

"The Use of Chlorhexidine/nPropyl Gallate (CPG) as a Urine Preservative", J.L. Nillen & S.M. Smith, Clinical Chemistry, vol. 42, #6, 1996, p. S310.*

"Urine Storage During Space Flight: A Comparison of Preservatives", J.E. Davis–Street, J. L. Nillen & S. M Smith, Clinical Chemistry, vol. 42. #6, 1996, p. S310.

* cited by examiner

Primary Examiner—Jill Warden
Assistant Examiner—Monique T. Cole
(74) Attorney, Agent, or Firm—James M. Cate

(57) ABSTRACT

Disclosed is CPG, a combination of a chlorhexidine salt (such as chlorhexidine digluconate, chlorhexidine diacetate, or chlorhexidine dichloride) and n-propyl gallate that can be used at ambient temperatures as a urine preservative.

15 Claims, No Drawings

URINE PRESERVATIVE

Statement as to Federally Siponsored Research

The work described herein was supported, at least in part, with funds from the Federal Government awarded through the National Aeronautics and Space Administration contract number NAS9-18492. Therefore, the Government may have certain rights in this invention.

BACKGROUND OF THE INVENTION

This invention relates to a urine preservative.

In monitoring the health of patients, urine is routinely collected and analyzed for analytes such as ammonia, calcium, urea nitrogen, sodium, potassium, and chloride. If the urine must be stored prior to analysis, precautionary measures should be taken to preserve the analytes in the urine. In the absence of a preservative, many analytes such as ammonia and calcium are unstable at room temperature. Other analytes are somewhat more stable. For example, urea, sodium, potassium, and chloride are stable for approximately 28 days, 7 months, 28 days, and 4 months, respectively. Although freezing the urine is a common method for preserving urine, freezing is not always a viable option. For example, in monitoring the health of crew members on board spacecraft, or patients in geographically remote areas, the availability of cold storage space typically is limited or unavailable.

Many of the previously described methods for preserving urine analytes at ambient temperatures do not preserve a broad spectrum of analytes and/or pose health risks. For example, strong acids such as concentrated hydrochloric acid and glacial acetic acid preserve few of the analytes present in urine. In spacecraft, the use of these acids is further limited because they impose a safety hazard to crew members. Furthermore, strong acids tend to alter the pH of the urine and negatively effect the analytes in urine. Other acids, such as diluted boric acid, pose few health hazards but ammonia remains unstable after treatment of urine with boric acid. Other compounds, such as thymol and thimerosal, have been used as urine preservatives; however, these compounds require special handling in order to alleviate safety concerns. In addition, ammonia remains unstable even after treatment of urine with thymol.

SUMMARY OF THE INVENTION

The invention features a urine preservative, termed CPG, that includes (i) a 10 to 20% (wt/vol) solution of a chlorhexidine salt (such as chlorhexidine digluconate, chlorhexidine diacetate, or chlorhexidine dichloride) and (ii) a 10 to 30% (wt/vol) solution of n-propyl gallate; the ratio of the chlorhexidine salt solution to the n-propyl gallate solution is 1:2 to 2:1. Generally, the chlorhexidine salt solution is a 20% aqueous solution. Typically, the n-propyl gallate solution is a solution of n-propyl gallate in methanol. Other solvents, such as water, any alcohol, can be substituted for methanol in producing the n-propyl gallate solution. Preferably, the solution of n-propyl gallate is a 20% (wt/vol) solution, and the ratio of n-propyl gallate to chlorhexidine salt is 1:1 (vol:vol).

Included within the invention is a method for producing a urine preservative; the method includes mixing a 10 to 30% (wt/vol) solution of n-propyl gallate with a 10 to 30 % solution of chlorhexidine salt at a ratio of 1:2 to 2: 1. Typically, the n-propyl gallate solution is a 20% solution (wt/vol) of n-propyl gallate (e.g., in methanol), while the chlorhexidine salt is a 20% aqueous solution. Generally, the n-propyl gallate solution is mixed with the chlorhexidine salt solution at a ratio of 1:1.

The invention also includes a method for preserving urine (e.g., human, primate, or dog, cat, or murine urine). This method includes mixing the urine preservative of the invention with urine to a concentration of 0.4 to 1.0 mg/ml of urine preservative in urine. Typically, the urine and urine preservative are mixed to produce a concentration of 0.4 mg/ml of urine preservative in urine.

The invention offers several advantages. For example, CPG allows the urine to be stored at room temperature, thus providing a convenient method for preserving and storing urine when freezer space is unavailable. In addition, CPG can be safely handled without the need for extensive precautionary measures. Also, CPG does not substantially alter the pH of the urine.

As used herein, the term "preserving" urine means treating urine (e.g., with CPG) to increase the stability of one or more analytes normally present in urine. Examples of such analytes include urea nitrogen (UN), creatinine, ammonia, calcium, sodium, potassium, chloride, osmolality, 3-methylhistidine, aldosterone, cortisol, cGMP, melatonin, and total nitrogen.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed descriptions, and from the claims.

DESCRIPTION OF THE PREFERRED EMBODIMENTS

Preparation of CPG

The urine preservative of the invention, termed CPG ( chlorhexidine salt/n-propyl gallate), can be prepared by mixing a chlorhexidine salt with n-propyl gallate. Chlorhexidine salt can be obtained from commercial suppliers. For example, chlorhexidine digluconate is available as a 20% aqueous solution (see, e.g., Sigma Chemical Company, St. Louis, Mo.; Catalog #C 9394). N-propyl gallate also is commercially available (see, e.g., Sigma Chemical Company, St. Louis, Mo.; Catalog #P 3130), and can be prepared as a 10 to 30% solution in a solvent such as absolute methanol, water, any alcohol. The chlorhexidine salt and n-propyl gallate then are mixed together at a ratio of 1:2 to 2:1. In a preferred method, CPG is produced by mixing a 20% solution of chlorhexidine digluconate (in water) with a 20% solution of n-propyl gallate (in absolute methanol) at a ratio of 1:1.

Preservation of Urine

Upon mixing CPG with urine, CPG acts as a urine preservative that inhibits decomposition of a broad spectrum of analytes in urine. Typically, CPG is mixed with urine within 2 hours, and preferably within 30 minutes, following completion of collection. For timed void periods (e.g., 24 hours), CPG is mixed with urine at the end of the collection period. When CPG is not mixed with urine immediately following urination, the urine typically will be chilled or frozen to inhibit decomposition of analytes prior to mixing the urine with CPG. Preferably, CPG and urine are mixed to yield a final concentration of 0.4 to 1.0 mg of CPG per milliliter of urine (e.g., 0.4 mg/ml). Upon mixing CPG with the urine, the urine/CPG mixture can be stored at room temperature; if desired, the urine/CPG mixture can be chilled (e.g., to 40° C.) or frozen (e.g., to −70° C.).

EXAMPLE

This example demonstrates that CPG increases the stability of analytes in urine. For this example, CPG was prepared by mixing a 20% solution of chlorhexidine digluconate with a 20% solution of n-propyl gallate at a ratio of 1:1 (vol:vol). CPG and urine were mixed to yield a final concentration of 0.4 mg/ml of CPG in urine. The urine was pooled from two separate sample collection types within two hours of completion of collection samples kept on ice up until collection was complete. An aliquot of the untreated urine was stored at −70° C., and an aliquot was stored at room temperature. A sample of the untreated urine was also stored at −70° C. The levels of analytes in the urine were measured on days 1, 14, and 28, and then once monthly for a total of 12 months. The length of stability of various analytes was determined and is listed in Table 1.

TABLE 1

LENGTH OF STABILITY OF URINE ANALYTES PRESERVED WITH CPG

| ANALYTE | LENGTH OF STABILITY (Compared to unpreserved urine stored at −70° C.) | |
| --- | --- | --- |
| | ROOM Temperature (no preservative) | Room Temperature (CPG preserved) |
| Urea | 28 days | 5 MONTHS |
| Ammonia | unstable | 14 DAYS |
| Calcium | unstable | 3 MONTHS |
| Creatinine | unstable | unstable |
| Sodium | 7 months | 7 months |
| Potassium | 28 days | 6 MONTHS |
| Chloride | 4 months | 4 months |
| Osmolality | unstable | unstable |
| 3-Methylhistidine | unstable | 2 MONTHS |
| Aldosterone | unstable | 14 DAYS |
| Cortisol | unstable | 2 MONTHS |
| cGMP | unstable | 7 MONTHS |
| Melatonin | 5 months | 8 MONTHS |
| Total Nitrogen | unstable | 3 MONTHS |

As is shown in Table 1, CPG treatment increased the stability of a broad spectrum of analytes in urine, such as urea, ammonia, calcium, potassium, 3-methylhistidine, aldosterone, cortisol, cGMP, melatonin, and total nitrogen. CPG also can increase the stability of other analytes such as the following (or analytes measured in the following tests): 17-Hydroxycorticosteroids, 17-ketogenic steroids, 17-ketosteroids, 3-methylhistidine, 5-Hydroxyindoleacetic Acid, alpha-amino acid nitrogen, alpha-1acid Glycoprotein, Acetone, Acetonitrile, Acrylonitrile, Adrenocorticotropic Hormone, Alanine, Albumin, Aldosterone, Aluminum, Ammonia chloride, Ammonia Nitrogen, Amphetamines, Amylase, Antimony, Arsenic, Barbiturates, Benzene, Benzodiazepines, Beryllium, Bilirubin, Bismuth, C-peptide, Cadmium, Calcium, Cannabinoids, Carbon Disulfide, Catecholamines, Chloride, Chromium, Cobalt, Cocaine, Copper, Coproporphyrin, Cortisol, Creatine, Cyclic AMP, Cystine, Dehydroepiandrosterone, Deoxypyridinoline, Estradiol, Estriol, Estrogens, Estrone, Ethylene glycol, Fluoride, Folate Absorption Test, Follicle Stimulating Hormone, Formaldehyde, Formiminoglutamic acid, Fructose, Galactose, Galactose Tolerance Test, Glucose, Glycine, Glycolic Acid, Gold, Hemocystine, Hemoglobin, Hemopexin, Homogentisic Acid, Homovanillic Acid, Hydroxyproline, Isoleucine, Ketones, 1-Lactate, Lactose, Lead, Leucine, Magnesium, Marijuana, Melanin, Mercury, Metanephrine, Methadone, Methanol, Methaqualone, Methionine, Mucopolysaccharide Screen, Myoglobin, n-telopeptide, Niacin, Nickel, Nitrites, Opiates, Oxylate, Pentachlorophenol, Pentazocine, Pentose, Phencyclidine, Phenols, Phenolsulfonphthalein Test, Phenylalanine, Phosphorus, Porphobilinogen, Potassium, Pregnancy test, Pregnanetriol, Propoxyphene, Protein, Pyridinoline, Pyruvic Acid, Riboflavin, Selenium, Sodium, Specific gravity, Sucrose, Testosterone, Tetrahydrocortisol, Tetrahydrodeoxycortisol, Thallium, Thiocyanate, Thyrotropin Releasing Hormone, Transferrin, Urea Nitrogen, Uric acid, Urobilinogen, Uroporphyrin, Valine, Vanillylmandelic Acid, and Vitamin C.

Other Embodiments

It is to be understood that, while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. A urine preservative comprising:
   (i) a 10 to 20% (wt/vol) solution of a chlorhexidine salt and
   (ii) a 10 to 30% (wt/vol) solution of n-propyl gallate, wherein the ratio of the chlorhexidine salt to the solution of n-propyl gallate is 1:2 to 2:1.

2. The urine preservative of claim 1, wherein the n-propyl gallate solution is a solution of n-propyl gallate in methanol.

3. The urine preservative of claim 1, wherein the n-propyl gallate solution is a solution of n-propyl gallate dissolved in a solvent selected from the group consisting of glycerol, water, alcohols, isopropanol, butanol, amylalcohol.

4. The urine preservative of claim 1, wherein the n-propyl gallate solution is a 20% (wt/vol) solution.

5. The urine preservative of claim 1, wherein the chlorhexidine salt solution is a 20% (wt/vol) solution.

6. The urine preservative of claim 1, wherein the ratio of n-propyl gallate to chlorhexidine salt is 1:1.

7. The urine preservative of claim 1, wherein the chlorhexidine salt is selected from the group consisting of chlorhexidine digluconate, chlorhexidine diacetate, and chlorhexidine dichloride.

8. A method for preserving urine, the method comprising mixing the urine preservative of claim 1 with urine to a concentration of 0.4 to 1.0 mg/ml of urine preservative in urine.

9. The method of claim 8, wherein the concentration of the urine preservative in urine is 0.4 mg/ml.

10. A method for producing a urine preservative, the method comprising mixing a 10 to 30% (wt/vol) solution of n-propyl gallate with a 10 to 20% (wt/vol) solution of chlorhexidine salt at a ratio of 1:2 to 2:1.

11. The method of claim 10, wherein the n-propyl gallate solution is a 20% (wt/vol) n-propyl gallate solution.

12. The method of claim 10, wherein the chlorhexidine salt solution is a 20% (wt/vol) solution.

13. The method of claim 10, wherein the n-propyl gallate solution is a solution of n-propyl gallate in methanol.

14. The method of claim 10, wherein the ratio of n-propyl gallate to chlorhexidine salt is 1:1.

15. The method of claim 10, wherein the chlorhexidine salt is selected from the group consisting of chlorhexidine digluconate, chlorhexidine diacetate, and chlorhexidine dichloride.

* * * * *